Figure 1:
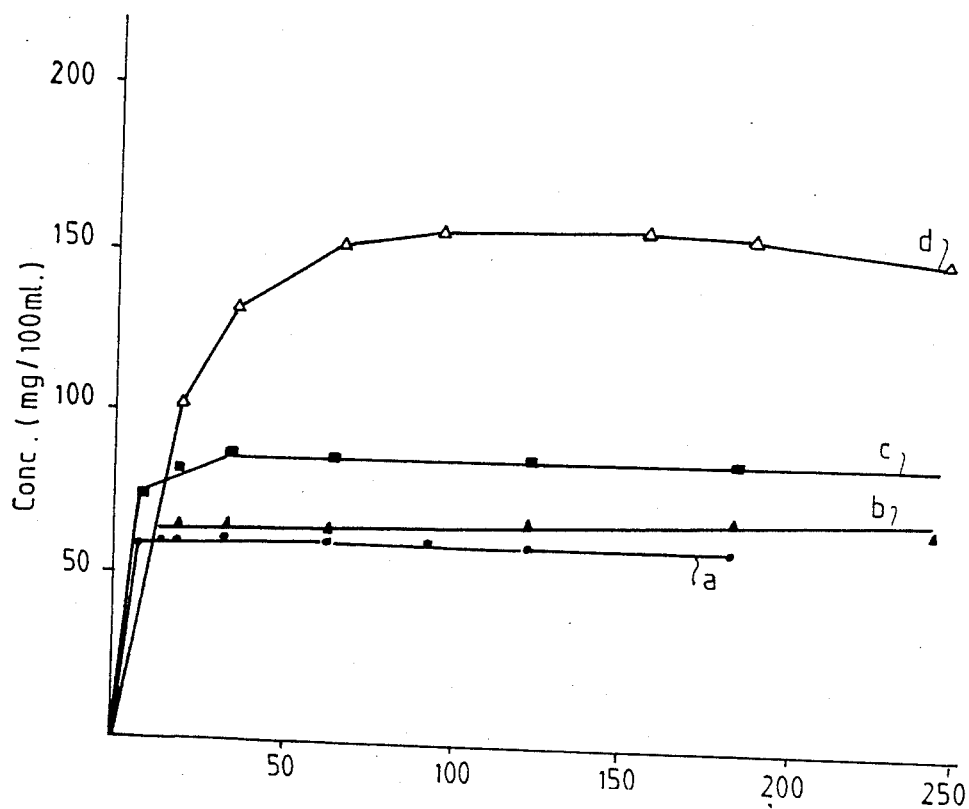

United States Patent [19]

Panoz et al.

[11] Patent Number: 4,610,875
[45] Date of Patent: Sep. 9, 1986

[54] MEDICAMENTS WITH A HIGH DEGREE OF SOLUBILITY AND METHOD FOR THEIR PRODUCTION

[75] Inventors: Donald E. Panoz, Athlone; Owen I. Corrigan, Howth, both of Ireland

[73] Assignee: Elan Corporation, P.L.C., Athlone, Ireland

[21] Appl. No.: 646,485

[22] Filed: Aug. 31, 1984

Related U.S. Application Data

[63] Continuation of Ser. No. 422,444, Sep. 23, 1982, abandoned.

[30] Foreign Application Priority Data

Apr. 19, 1982 [FR] France ................... 82 06646

[51] Int. Cl.⁴ .................. A61K 31/79; A61K 9/00; A61K 31/505
[52] U.S. Cl. ........................................... 424/80
[58] Field of Search ............................. 424/80

[56] References Cited

U.S. PATENT DOCUMENTS

| | | | |
|---|---|---|---|
| 4,127,647 | 11/1978 | Sato et al. | 424/78 |
| 4,151,273 | 4/1979 | Riegelman et al. | 424/78 |
| 4,327,080 | 4/1982 | Wong et al. | 424/80 |
| 4,343,789 | 8/1982 | Kawata et al. | 424/78 |
| 4,344,934 | 8/1982 | Martin et al. | 424/80 |
| 4,404,183 | 9/1983 | Kawata et al. | 424/19 |
| 4,562,069 | 12/1985 | Hegasy et al. | 424/80 |

FOREIGN PATENT DOCUMENTS 0003682 8/1979 European Pat. Off. .

OTHER PUBLICATIONS

Newton, J. M., "Spray Drying and Its Application in Pharmaceuticals", *Manufacturing Chemist and Aerosol News*, pp. 33-36 (Apr., 1966).
Keiji Yamamoto, et al, "Dissolution Behavior and Bioavailability of Phenytoin from a Ground Mixture with Microcrystalline Cellulose," J. Pharm. Sci., 65 (10) at 1484-1488 (Oct. 1976).
Chem. Abstract 95: 156593+(1981) re: Japan 81 55370.
Patent Abstract Japan Appl. No. 54-123216 (4-28-81).
Kuhnert et al, C.A. 97:28495s (1982) of Sci. Pharm. 1982 50(1):3-11.
Kuhnert et al, C.A. 98:132438q (1983) of Sci. Pharm. 1982 50(4):324-331.
Elan Corp. Ltd., C.A. 99:76892q (1983) of Belg. 894942, 09 May 1983.
Luger, C.A. 99:167375q (1983) of Acta Crystallorg. Sect. C: Cryst. Struct. Commun. 1983, C3g(10), 1454-8.
Haleblian Chem. Abstr. 83: 136757y (1975) of J. Pharm. Sci. (1975) 64(8):1269-1288, Characterization of Habit and Crystalline Modification of Solids and Their Pharmaceutical Applications.
Beyer, C.A. 89 #152645Q (1978) of Acta Pharm. Technol. (1978) 24(2):171-174.
Kala et al, C.A. 95 #12664u (1981) of Pharmazie (1981) 36(2):106-111.
Nuernberg et al, C.A. 91 #9445k (1979) of Acta Pharm. Technol. (1979) 25(1):49-63.
Junginger, C.A. 85 #130430f (1976) of Pharm. Ind. (1976) 38(5):461-471.
Arita et al, C.A. 92 #135314a (1980) of Gekkan Ryuichi (1979) 21(12):2737-45.
Moriyama et al, C.A. 85 #123640w (1976) of Japan Kokai 76 63925, 02 Jun. 1976.
Nuernberg, C.A. 86 #86034 (1977) of Prog. Colloid. Polym. Sci. (1976) 59:55-69.
Lippold et al, C.A. 89 #12145b (1978) of Ger. Offen. 2,634,004, 02 Feb. 1978.

(List continued on next page.)

*Primary Examiner*—Shep K. Rose
*Attorney, Agent, or Firm*—Robert Hardy Falk; Randall C. Brown

[57] ABSTRACT

The present invention relates to medicaments with a high degree of dissolution rate and solubility. These medicaments are characterized in that they are in amorphous form produced by spraying in the presence of a stabilizer and of an agent inhibiting the formation of crystals.

1 Claim, 2 Drawing Figures

OTHER PUBLICATIONS

Stupa et al, C.A. 83 #15575d (1975) of J. Pharmaco. Biopharm. 192 2(61):511–524.

O. I. Corrigan and E. M. Holohan, "Amorphous Spray-Dried Hydroflumethiazide-Polyvinylpyrrolidone Systems: Physicochemical Properties," J. Pharm. Pharmacol, 1984, 36:217–221.

A. A. Badawi and A. A. El-Sayed, "Dissolution Studies of Povidone-Sulfathiazole Coacervated Systems", J. Pharm. Sci. 69:492–497 (1980).

Win L. Chiou and Leslie Ekyle, "Differential Thermal, Solubility, and Aging Studies on Various Sources of Digoxin and Digitoxin Powder:Biopharmaceutical Implications", J. Pharma. Sci. 68:1224–1229 (1979).

Win L. Chious and Sidney Riegelman, "Pharmaceutical Applications of Solid Dispersion Systems", J. Pharma. Sci. 60: 1281–1301 (1971).

O. I. Corrigan, M. A. Farvar, and W. I. Higuchi, "Drug Membrane Transport Enhancement Using High Energy Drug Polyvinylpyrrolidone (PVP) Co-Precipitates, Int. J. Pharma. 5:229–238 (1980).

O. I. Corrigan, K. Sabra, and E. M. Holohan, "Physicochemical Properties of Spray Dried Drugs: Phenobarbitone and Hydroflumethiazide", Drug. Dev. Indust. Pharm. 9:1–20 (1983).

O. I. Corrigan, and R. F. Timoney, "The Influence of Polyvinylpyrrolidone on the Dissolution Properties of Hydroflumethiazide", J. Pharm. Pharmacol. 27:759–764 (1975).

H. J. de Nordwall and L. A. K. Staveley, "The Formation and Crystallization of Simple Organic and Inorganic Glasses", Trans. Faraday Soc. 52:1207–1215 (1956).

Hitoshi Sekikawa, Masahiro Nakano, and Takaichi Arita, "Dissolution Mechanisms of Drug-Polyvinylpyrrolidone Coprecipitates in Aqueons Solution", Chem. Pharm. Bull. 27:1223–1230 (1979).

Eli Shefter and K. C. Cheng, "Drug-Polyvinylpyrrolidone (PVP) Dispersions—A Differential Scanning Colorimetric Study", Int. J. Pharm. 6:179–182 (1980).

A. P. Simonelli, S. C. Mehta, and W. J. Higuchi, "Dissolution Rates of High Energy Sulfathiazide—Povidone Coprecipitates II: Characterization of Form of Drug Controlling Its Dissolution Rate via Solubility Studies", J. Pharm. Sci. 65:355–360 (1976).

A. P. Simonelli, S. C. Mehta, and W. I. Higuchi, "Dissolution Rates of High Energy Polyvinylpyrrolidone (PVP)-Sulfathiazole Coprecipitates", J. Pharm. Sci. 58:538–548 (1969).

M. P. Summers, "Glass Formation in Barbiturates and Solid Dispersion Systems of Barbiturates with Citric Acid", J. Pharma. Sci. 67:1606–1610 (1978).

MEDICAMENTS WITH A HIGH DEGREE OF SOLUBILITY AND METHOD FOR THEIR PRODUCTION

This application is a continuation of application Ser. No. 422,444, filed Sept. 23, 1982, now abandoned.

The present invention relates to medicaments with a high degree of dissolution rate and solubility and to a method for their production.

It is known and widely demonstrated that the dissolution rate and solubility of a medicament represents a determining factor in its therapeutic activity. It is known that therapeutic activity depends on the bio-availability of the medicament, which is a function of good and/or complete absorption. The latter depends on the degree of dissolution of the active principle forming the medicament. The good dissolution of a medicament is all the more indispensable as there exists a certain and very limited area of the gastro-intestinal tract adapted to absorb the medicament and the non-availability of a medicament following its poor or incomplete dissolution in contact with this area causes poor absorption and, thereby, a therapeutic action which ranges from reduced to very variable. It should be added also that a high degree of solubility of a medicament enables the preparation, if desired, of concentrated liquid forms. Now the liquid form of a medicament enables the posology to be easily varied, lends itself to coloring, to sweetening and to the aromatization of the medicament vehicle. Once diluted, medicaments are less irritating than in cachets, powders, tablets or pills, pharmaceutical forms which place them in direct contact with the mucuous membranes, at which local irritation of the gastric mucuous tissue can occur. Sometimes, the liquid form is indispensable as, for example, for hygroscopic products and liquid eutectic mixtures which cannot be put into powders or cachets.

It is known that crystalline forms (the most stable forms) are those which dissolve with most difficulty; thus for a long time attempts have been made to prepare medicaments containing the active principles in amorphous form, of which form the solubility is higher than that of the crystalline form (see review of J. Haleblain, J. Pharm. Sci. 64, 1269 (1975)). However, these amorphous forms present the problem that they are converted readily in time into crystalline forms, i.e., amorphous forms may not be physically stable, which is a very serious drawback for maintaining the enhanced dissolution of a substance for therapeutic use.

Accordingly it is an object of the present invention to provide a medicinal form with a high degree of solubility and dissolution, preserving a physical and chemical stability necessary for any medicament.

According to the invention there is provided a medicament with a high degree of solubility characterized in that it is in amorphous form obtained by spraying in the presence of a stabilizer and of an agent inhibiting crystal formation.

According to an advantageous embodiment of the present invention, the stabilizer and the crystal-formation inhibiting agent are constituted by polyvinylpyrrolidone.

According to another advantageous embodiment of the present invention, the inhibiting agent is constituted by the mixture polyethyleneglycol-polyvinylpyrrolidone.

According to the invention the concentration of the inhibiting agent present at the time of spraying is comprised between 1 and 50% with respect to the active principle (weight/weight).

The amount of stabilizer and of crystal formation inhibiting agent added before the spraying is of course a function of the nature of the active principle utilized. The more physically unstable the medicinal substance in the amorphous phase or the more it tends to form crystals, the greater is the amount of inhibiting polymer added.

The inhibiting polymer must be added before the spraying of the medicament, since the simple mixing of the inhibitor with the active principle sprayed alone, without the inhibitor, leads to a product whose solubility dissolution characteristics are, by a long way, inferior to those obtained with the products according to the present invention.

Moreover, numerous analyses, and particularly differential scanning calorimetry (DSC) carried out by Applicant have enabled it to be envisaged that a large part of the medicinal substance is in the form of an amorphous drug: i.e., the medicinal substance-polyvinylpyrrolidone.

According to another aspect of the present invention, there is provided a process for the preparation of medicaments, characterized in that the active principle and the inhibiting polymer are dissolved in a solvent, with heating if necessary, then atomized in a sprayer, the input and output temperatures being comprised respectively between 110° and 150° C. and 80° to 120° C.

According to an advantageous embodiment of the method according to the present invention, the solvent for dissolving the active substance and the inhibitor is constituted by water and/or a low molecular weight alcohol ($C_1$ to $C_4$).

According to another advantageous embodiment, the process according to the present invention is a process for the preparation of a stable pharmaceutical dipyridamole composition with a high dissolution rate in the gastrointestinal tract, in which dipyridamole is in amorphous form, comprising the steps of:

(a) dissolving amorphous crystalline dipyridamole in a pharmaceutically acceptable solvent constituted by water, a low molecular weight $C_1$ to $C_4$ alcohol, or mixtures thereof, with a stabilizing and crystal-formation-inhibiting amount of 5% w/w to 35% w/w of polyvinylpyrrolidone with respect to the weight of the dipyridamole;

(b) heating said solution to about 110° to about 150° C.; and (c) atomizing said heated solution at an input temperature of about 110° to about 150° C. in a sprayer such that the output temperature is between about 80° and about 120° C., to obtain stable amorphous dipyridamole-polyvinylpyrrolidone.

Apart from the foregoing features, the invention also comprises other features which will emerge from the description which follows.

The present invention will be better understood by means of the additional description which follows, in which examples of the preparation of novel medicaments according to the present invention are given, as well as the characteristics of the various products obtained.

It must be well understood, however, that these examples are given purely by way of illustration of the invention of which they do not constitute in any way a limitation thereof.

EXAMPLES OF THE PREPARATION

Example 1

Preparation of hydroflumethiazide

In 50 parts of ethanol are dissolved 1 part of hydroflumethiazide and 0.1 parts of polyvinylpyrrolidone. This solution is then atomized (for example in a BUCHI 190 apparatus). The feed temperature is adjusted to 132° and the output temperature to 98° C. Atomizing flow rate: 750 ml/hour.

FIG. 1 shows the solubility graphs of unatomized hydroflumethiazide (graph a), hydroflumethiazide atomized in the absence of PVP (graph b), hydroflumethiazide atomized but mixed with 10% of PVP (graph c), hydroflumethiazide atomized according to Example 1 (graph d), It is clearly seen that the process according to the present invention enables the solubility of the medicament to be considerably increased, while the latter is much less affected by a simple hydroflumethiazide+PVP mixture.

The product obtained according to Example 1 is practically unchanged in structure over at least four months, while a sample of hydroflumethiazide atomized without the presence of PVP is converted entirely into the crystalline form at the end of 12 days.

Example 2

Preparation of dipyridamole

Procedure was as described in Example 1, but solutions containing 0%, 5%, 10%, 20% and 35% of PVP with respect to the weight of dipyridamole, were prepared and then atomized.

Figure 2:
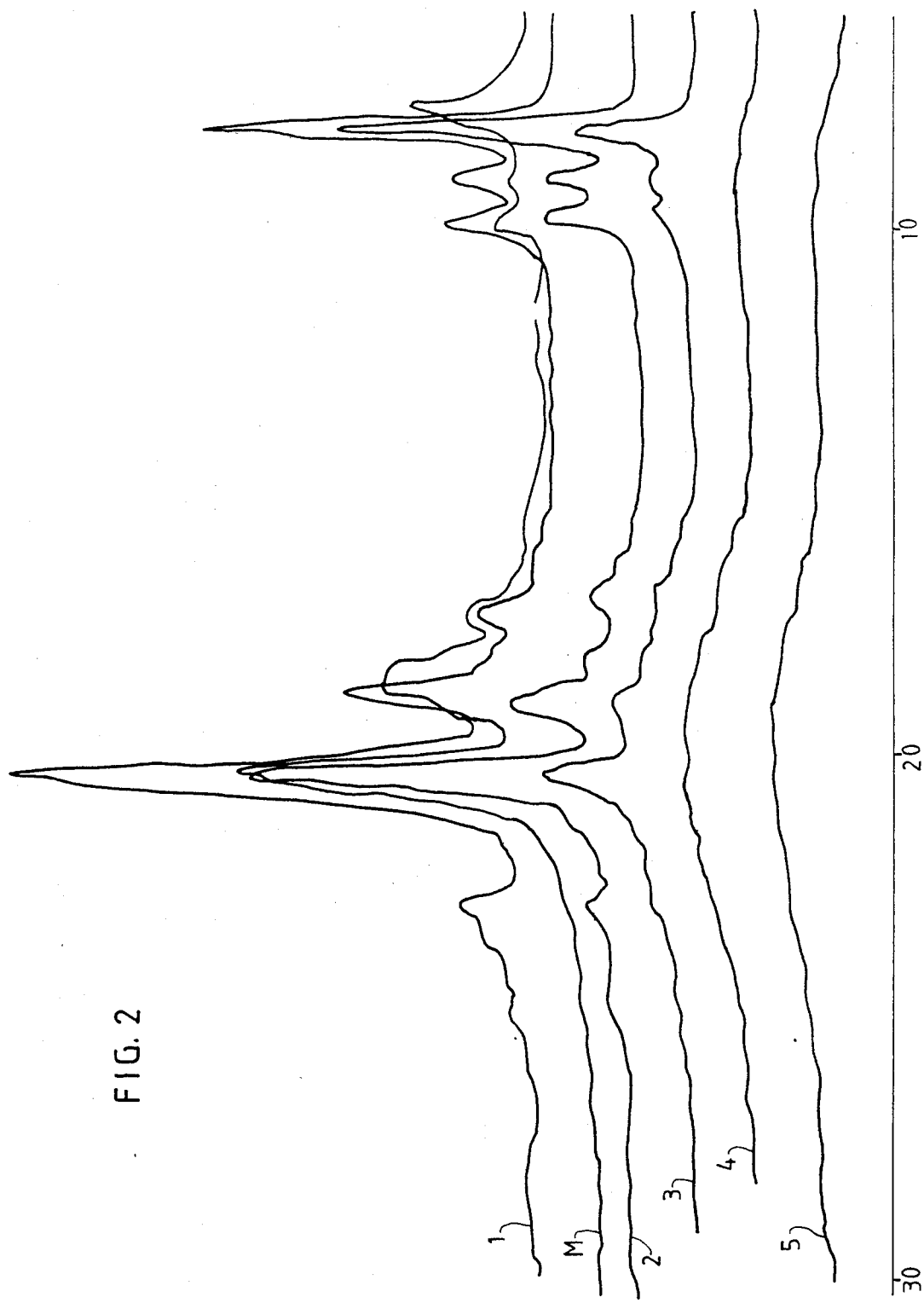

FIG. 2 shows the X-ray diffraction curves of the different products obtained. It is to be noted that the diffraction curve of the mixture dipyridamole-PVP 3:1 (curve M) has an entirely different shape from the curve 5.

Curve 1 represents 0% of PVP.
Curve 2 represents 5% of PVP.
Curve 3 represents 10% of PVP.
Curve 4 represents 20% of PVP.
Curve 5 represents 35% of PVP.

The solubility of the product represented by curve 5 is twice greater than that of the mixture M.

Examples 3 to 25

Results as interesting as those described in Examples 1 and 2 were obtained by utilizing the following medicaments: hydrochlorthiazide, cyclothiazide, cyclopenthiazide, polythiazide, methyldopa, spironolactone, quinidine, cyanidol, metronidazole, ibuprofen, naproxen, erythromycin, glaphenin, furosemide, suloctidil, nitrofurantoin, indomethacin, flavoxate, phenobarbital, cyclandelate, ketoprofen, naftidrofuryl and triamterene.

It results from the foregoing description that whatever the types of application and embodiments adopted, medicaments which are stable over time and of complete solubility are obtained, much superior to that of previously known medicaments.

Thus as emerges from the foregoing, the invention is in no way limited to those of its types of application, embodiments and uses which have just been described more explicitly; it encompasses thereof on the contrary all modifications which may come to the mind of the technician skilled in the art, without departing from the scope, nor the range, of the present invention.

We claim:

1. A process for the preparation of a stable pharmaceutical dipyridamole composition with a high dissolution rate in the gastrointestinal tract, in which dipyridamole is in amorphous form, comprising the steps of:
    (a) dissolving non-amorphous crystalline dipyridamole in a pharmaceutically acceptable solvent constituted by water, a low molecular weight $C_1$ to $C_4$ alcohol, or mixtures thereof, with a stabilizing and crystal-formation-inhibiting amount of 5% w/w to 35% w/w of polyvinylpyrrolidone with respect to the weight of the dipyridamole;
    (b) heating said solution to about 110° to about 150° C.; and
    (c) atomizing said heated solution at an input temperature of about 110° to about 150° C. in a sprayer such that the output temperature is between about 80° and about 120° C., to obtain stable amorphous dipyridamole-polyvinylpyrrolidone.

* * * * *

UNITED STATES PATENT AND TRADEMARK OFFICE
CERTIFICATE OF CORRECTION

PATENT NO. : 4,610,875

DATED : September 9, 1986

INVENTOR(S) : Donald E. Panoz et al.

It is certified that error appears in the above-identified patent and that said Letters Patent is hereby corrected as shown below:

Column 1, line 54, the language "dissolution," should read — dissolution, while —.

Column 2, line 24, the language "drug: i.e., the" should read — complex: —.

Column 3, line 19, the comma should be a period.

Signed and Sealed this

Seventeenth Day of February, 1987

Attest:

DONALD J. QUIGG

Attesting Officer     Commissioner of Patents and Trademarks